(12) United States Patent
Signorile et al.

(10) Patent No.: US 9,861,711 B2
(45) Date of Patent: Jan. 9, 2018

(54) LABELED LIGANDS OF ANTI-MULLERIAN HORMONE FOR DIAGNOSIS OF ENDOMETRIOSIS

(71) Applicants: Pietro Giulio Signorile, Rome (IT); Alfonso Baldi, Naples (IT)

(72) Inventors: Pietro Giulio Signorile, Rome (IT); Alfonso Baldi, Naples (IT)

(*) Notice: Subject to any disclaimer, the term of this patent is extended or adjusted under 35 U.S.C. 154(b) by 0 days.

(21) Appl. No.: 14/910,683

(22) PCT Filed: Aug. 4, 2014

(86) PCT No.: PCT/IB2014/063673
§ 371 (c)(1),
(2) Date: Feb. 5, 2016

(87) PCT Pub. No.: WO2015/019269
PCT Pub. Date: Feb. 12, 2015

(65) Prior Publication Data
US 2016/0184463 A1    Jun. 30, 2016

(30) Foreign Application Priority Data
Aug. 5, 2013 (IT) .............................. RM2013A0455

(51) Int. Cl.
| A61K 49/04 | (2006.01) |
| A61K 49/14 | (2006.01) |
| A61K 51/08 | (2006.01) |
| A61K 51/10 | (2006.01) |
| C07K 16/26 | (2006.01) |
| A61K 49/16 | (2006.01) |
| A61K 47/64 | (2017.01) |
| A61K 47/68 | (2017.01) |

(52) U.S. Cl.
CPC .......... *A61K 49/16* (2013.01); *A61K 47/6425* (2017.08); *A61K 47/6847* (2017.08); *A61K 49/0438* (2013.01); *A61K 49/14* (2013.01); *A61K 51/088* (2013.01); *A61K 51/1024* (2013.01); *A61K 51/1096* (2013.01); *C07K 16/26* (2013.01); *C07K 2317/40* (2013.01)

(58) Field of Classification Search
None
See application file for complete search history.

(56) References Cited

U.S. PATENT DOCUMENTS

| 2006/0275850 A1 | 12/2006 | Groome et al. |
| 2010/0135996 A1* | 6/2010 | Teulon ............... C07K 16/2869 424/133.1 |

FOREIGN PATENT DOCUMENTS

| WO | 95/16709 | 6/1995 |
| WO | 2006/127850 | 11/2006 |
| WO | WO2008/053330 | * 5/2008 |
| WO | 2008/153433 | 12/2008 |
| WO | 2009/052119 | 4/2009 |

OTHER PUBLICATIONS

Signorile and Baldi, J. Cell. Physiol. 2015; 230: 1270-1275.*
Kornguth et al., J Neurosurg. 1987; 66: 898-906.*
Int'l Search Report for PCT/IB2014/063673, four pages (dated Sep. 2014).
Written Opinion of ISA for PCT/IB2014/063673, seven pages (dated Sep. 2014).
Griffin et al. "Radiology of Benign Disorders of Menstruation" *Seminars in Ultrasound, CT and MRI*, vol. 31, No. 5, pp. 414-432 (Oct. 2010).
Namkung et al. "Mullerian inhibiting substance induces apoptosis of human endometrial stromal cells in endometriosis" *Journal of Clinical Endocrinology and Metabolism*, vol. 97, No. 9, pp. 3324-3230 (Sep. 2012).

* cited by examiner

*Primary Examiner* — Christina M Borgeest
(74) *Attorney, Agent, or Firm* — Nixon & Vanderhye PC

(57) ABSTRACT

The present invention relates to isolated ligands of anti-Mullerian hormone marked so as to be directly detectable by means of magnetic resonance imaging in the endometriosic lesions. In particular, such ligands can be used in a method for diagnosing in vivo endometriosis wherein said method comprises a passage of localizing and/or evaluating the entity of the endometriosic lesions in a patient.

8 Claims, 3 Drawing Sheets

LABELED LIGANDS OF ANTI-MULLERIAN HORMONE FOR DIAGNOSIS OF ENDOMETRIOSIS

Figures 1A, 1B:
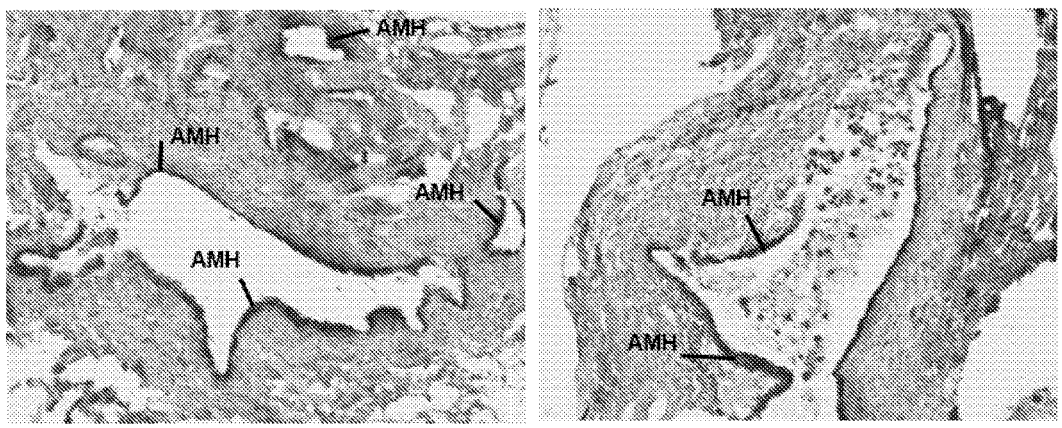

This application is the U.S. national phase of International Application No. PCT/IB2014/063673, filed 4 Aug. 2014, which designated the U.S. and claims priority to Italian Application No. RM2013A000455, filed 5 Aug. 2013; the entire contents of each of which are hereby incorporated by reference.

The present invention relates to isolated ligands of anti-Mullerian hormone labeled so as to be directly detectable by means of imaging techniques in the endometriosis lesions. In particular, such ligands can be used in a method for the in vivo diagnosis of endometriosis wherein said method comprises a passage of localizing and/or evaluating the entity of the endometriosic lesions in a patient.

STATE OF PRIOR ART

Endometriosis is defined as a recurrent and benign gynaecological disorder characterized by the presence of endometrial tissue (glands and stroma) outside the cavity of uterus. It is one of the most common diseases in the gynaecological field, affecting about 10% of the female population in reproductive age, whereas its frequency rises up to 20-50% in women with fertility problems (Baldi A. et al. Endometriosis: pathogenesis, diagnosis, therapy and association with cancer. Oncology Reports 2008; 19:843-846).

The endometriosis neoformations mainly are localized on the pelvic peritoneum and ovaries, but they can be commonly found in the sub-peritoneal areas and, more rarely, in any anatomic region, such as for example pericardium, pleurae, pulmonary parenchyma and even brain (Giudice L C, and Kao L C: Endometriosis. The Lancet, 364: 1789-1799, 2004; Signorile P G et al. Rectovaginal septum endometriosis: an immunohistochemical analysis of 62 cases. In Vivo 2009; 23:459-464).

The pathogenesis of such disease is still unknown; the most reliable hypotheses are retrograde menstruation and coelomic metaplasia (Gazvani R. & Templeton A. New considerations for the pathogenesis of endometriosis. Int. J. Gynaecol. Obstet. 2002; 76:117-126; Slater M. et al. Endometriotic cells exhibit metaplastic change and oxidative DNA damage as well as decreased function, compared to normal endometrium. J. Mol. Histol. 2005; 36:257-263; Starzinski-Powitz A. et al. In search of pathogenic mechanisms in endometriosis: the challenge for molecular cell biology. Curr. Mol. Med. 2001; 1:655-664.).

Recently the presence of endometriosis lesions in the female foetus has been described and this represents the first demonstration of a different pathogenetic theory based upon defects of embryogenesis (Signorile P G, Baldi A: Endometriosis: new concepts in the pathogenesis. Int J Biochem Cell Biol 2010; 42:778-780).

The anti-Mullerian hormone (AMH) is a glycoprotein belonging to the superfamily of the "Transforming Growth Factor-beta" (TGF-beta). The AMH is produced by the cells of the Sertoli in the male foetus and it is responsible for the regression of the Mullerian ducts (La Marca A et al.: Anti-Mullerian hormone (AMH): what do we still need to know? Hum Reproduct, 24: 2264-2275, 2009). The AMH expression in the ovarian follicles starts in the female foetus, around the 32th week of gestation and keeps for the woman's whole fertile life. The AMH expression levels are considered good indicators of a woman's ovarian reserve; they decay with menopause (Lee M M et al.: Mullerian inhibiting substance in humans: normal levels from infancy to adulthood. J Clin Endocrinol Metab, 81: 571-576, 1996). Furthermore, an anti-cancer action for AMH has been proposed in the ovarian epithelial tumours and different experimental proofs seem supporting the cytotoxic effect on tumour cells (La Marca A., Volpe A: The anti-Mullerian Hormone and ovarian cancer. Hum Reproduct., 13: 265-273, 2007). Recent studies have demonstrated that AMH, as well as a receptor thereof (MISRII), are expressed in the adult woman even at the level of endometrium, wherein probably they perform a paracrine type function.

Up to now no marker has been described allowing localizing exactly in vivo the endometriosis lesions, both cystic and connective solid ones. In particular, several of the endometriosis neoformations can even have very reduced sizes (smaller than 1 cm), which makes it practically impossible, with the currently available analysis methods, to highlight in vivo the localization both of cystic endometriosis lesions smaller than two millimeters and of the connective solid lesions smaller than one centimeter.

Still nowadays endometriosis is a disease therefor the one and only effective therapeutic strategy is the surgical removal of the endometriosic lesions: there is no resolving pharmacological therapy and the only pharmacological treatments used by the medical-scientific community are able only to act on symptoms, by relieving them. However, the success of the surgical procedure is substantially based upon the possibility of displaying in vivo the endometriosis lesion, which display is strictly connected even to the size of the lesion itself. It follows that, the effectiveness of the surgical treatment is limited by the fact that, as the disease is multicentric and often microscopic, the surgeon not always succeeds in eliminating all disease foci.

Therefore, in the state of art there is a highly felt need for detecting procedures allowing one to obtain a precise picture regarding the localization and the sizes of the disease's different foci (endometriosis formations) in the patient, so as to be able to diagnose and intervene in the most effective way in patients with endometriosis even in the states wherein the lesions have very reduced sizes.

The scope of the present invention is to overcome the problems associated to the detection of endometriosis formations and, in particular, of the endometriosis neoformations, so as to develop alternative methods for diagnosing and/or treating endometriosis.

SUMMARY OF THE INVENTION

The present invention relates to isolated ligands of anti-Mullerian hormone marked so as to be directly detected in the endometriosis lesions by means of magnetic resonance imaging. In particular, such ligands can be used in an in vivo method for diagnosing endometriosis including a step of localizing and/or evaluating the entity of the endometriosis lesions in a patient.

The invention subject of the present description is based upon the scientific observation, made by the inventors themselves, that the anti-Mullerian hormone (AMH) is over-expressed in the endometriosis lesions as shown in FIG. 1. From such observation derives the intuition of the inventors of being able to use AMH as target to detect foci (formations and/or neoformations) of the endometriosis disease.

In particular, as highlighted in the section "Examples", it was demonstrated that AMH can be used in an effective way as a cellular target to allow the detection in vivo the exact localization of the endometriosis lesions. In fact, as shown in example 2 herebelow, a xenotransplant of human endometriosis tissue in nude mice can be subsequently shown by means of using a labeled ligand such as, for example, a labeled anti-AMH antibody so as to be able to be detected by means of in vivo magnetic resonance imaging techniques (FIGS. 2 and 3).

In particular, the use of a ligand able to link AMH, labeled so as to be able to be detected by means of magnetic resonance imaging in vivo techniques, demonstrated to be effective in detecting not only the endometriosis lesions with appreciable sizes but even anatomic localizations of endometriosis with small sizes, lower than 0.5 centimeters of diameter. These data suggest that the ligand of the invention can be used advantageously not only for localizing the lesions but even for evaluating, by means of the sizes of the lesions themselves, the entity/gravity of endometriosis.

It follows that the ligand of the invention can be used even for learning the real extension of the endometriosis disease since the intra-organ lesions, which are not detectable by surgery, can be effectively localized too before performing the operation.

From what is said above, it appears clear that the use of the anti-AMH antibody of the invention can make the steps of diagnosing endometriosis and/or surgical treatment of the pathology more selective and effective by defining the precise localization and extension of the endometriosis lesions.

Furthermore, as the here described approach is not invasive since it mainly consists of administrating the ligand able to bind AMH to the patient and displaying in vivo the sites wherein it accumulates as consequence of binding to AMH deposits, the ligand of the invention can be advantageously used even to monitor in time the progress of endometriosis pathology such as, for example but not only, in case the patient is subjected to schemes of pharmacological and/or surgical therapies.

Therefore the subject of the present application is:
the isolated ligand of anti-Mullerian hormone suitable to be detected directly by means of magnetic resonance imaging for use in a in vivo method of diagnosing endometriosis comprising a step of localization and/or evaluation of the entity of the endometriosis lesions in a patient;
a formulation for use in a in vivo method of localizing and/or evaluating the entity of the endometriosis lesions in a patient comprising a ligand according to the invention and at least pharmaceutically acceptable carrier and/or excipient;
kit for localizing and/or evaluating in vivo the entity of the endometriosis lesions in a patient comprising at least a ligand of the invention or a formulation of the invention and means useful to administer said ligand or said formulation to said patient.

Additional advantages, as well as the features and the use modes of the present invention will result evident from the following detailed description of some preferred embodiments, shown purely by way of example and not with limitative purpose.

DETAILED DESCRIPTION OF THE FIGURES

FIGS. 1A and 1B: Examples of AMH hormone expression in the in vivo endometriosis structures, by means of an immunohistochemical method; the AMH expression is detected by staining of intense dark colour.

Figure 2A:
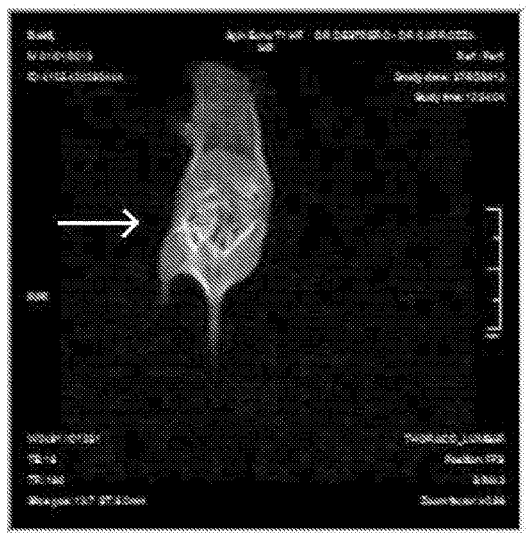
Figure 2B:
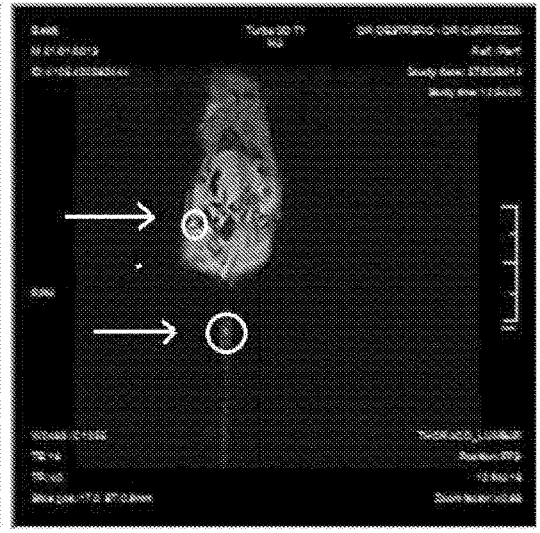
Figure 3A:
Figure 3B:

FIGS. 2A and 2B: Total-body Magnetic Resonance Image of a small female mouse before (FIG. 2A) and after (FIG. 2B) the inoculation of gadolinium-conjugated antibody against AMH: the area corresponding to the subcutaneous ectopic transplant of connective solid endometriosis tissue and the tail area wherein the inoculation of the gadolinium-antibody compound for AMH took place are circled in white, FIGS. 3A and 3B: Magnetic Resonance Image in cross-section of a female mouse before (FIG. 3A) and after (FIG. 3B) the inoculation of gadolinium-conjugated antibody against AMH: the area corresponding to the ectopic transplant is circled in white, FIG. 4A-4D: histological and immunohistochemical analysis of the transplanted tissue. FIGS. 4A and 4B show the histological structure of the transplant with colouring by means of Hematoxylin-Van Gieson and Hematoxylin-Eosin; FIGS. 4C and 4D show the expression (immunohistochemical staining of intense black colour), respectively of CD10 and AMH in the transplanted tissue.

DETAILED DESCRIPTION OF THE INVENTION

The present invention, as already shown in the previous section, relates to an isolated ligand of the labeled anti-Mullerian hormone (AMH) able to be detected by means of magnetic resonance imaging in the endometriosis lesions.

Under ligand of the anti-Mullerian hormone (Ab anti-AMH) in the present invention a natural or synthetic molecule is meant, able to bind, preferably with high affinity, at least a specific epitope of AMH protein.

As it is known to the person skilled in the art the term epitope or antigenic determinant relates to a site on the antigen, in this case the AMH protein, which is specifically recognized and bind by an immunoglobulin. The epitopes can be formed by a sequence of contiguous amino acids or by juxtaposed amino acids in the three-dimensional shape of the protein. Preferably the ligand of the present invention is able to link an AMH epitope not present in other proteins, so as to avoid nonspecific binding to proteins different from anti-Mullerian hormone.

Anti-Mullerian hormone is a glycated protein of homodimeric 140 kDa belonging to the superfamily of the "Transforming Growth Factor-beta" (TGF-beta). The nucleotidic sequence and the coding amino acid sequence for AMH of different origins (human, murine, bovine) is described in the known state of art. In particular, the amino acid sequence of the monomeric AMH of human origin (sequence of 535 aa) is described in the database UniProtKB/Swiss-Prot, version 133, last modification 16 May 2012; http://www.uniprot.org/) and identified with number P03971.

Preferably, the ligand of the invention is able to recognize and bind an epitope of human anti-Mullerian hormone.

In an embodiment, the ligand of the invention can be an antibody or a receptor able to bind in a specific way at least an epitope of the AMH hormone. By way of example and not for limiting purpose, the isolated receptor to be used as ligand according to what is described herein is the receptor of type II of the anti-Mullerian hormone (MISIIR) (The Mülledan duct: recent insights into its development and regression Klattig J, Englert C. Sex Dev. 2007; 1(5):271-8).

Under the term "antibody" in the present invention complete antibodies, antibodies with single chain, synthetic antibodies, chimeric antibodies, humanized antibodies, non-human antibodies, conjugates of antibodies and fragments or their derivatives are meant. In particular, under "complete antibodies" in the present invention proteins or glycoproteins are referred to, comprising at least two heavy chains and at least two light chains inter-connected by means of disulphide bridges.

Each heavy chain is composed of a variable region ($V_H$) and a constant region ($C_H$). The constant region ($C_H$) comprises three domains $C_H1$, $C_H2$ and $C_H3$.

Each light chain is composed of a variable region ($V_L$) and a constant region ($C_L$). The variable regions of the heavy chain ($V_H$) and of the light chain ($V_L$) can be further divided into hypervariable regions known as "Complementarity determining regions" (CDR). Such regions CDR are hypervariable with respect to the more preserved regions known as Framework region (FR). Each $V_H$ and $V_L$ is composed of 3 CDR and four FR, arranged from the terminal amino end to the terminal carboxy end in the following order: FR1, CDR1, FR2, CDR2, FR3, CDR3, FR4. The variable regions of the light and heavy chains contain the domain interacting with the antigen, by binding it. By way of pure example, such fragment can be: a Fab fragment consisting of the domains $V_L$, $V_H$, $C_L$ and $C_H1$; a fragment consisting of the domains $V_H$ and $C_H1$; a Fv fragment consisting of domains $V_L$ and $V_H$; a fragment consisting of a single variable domain isolated by a CDR region; F(ab')2 fragment comprising two linked fragments Fab; Fv molecules with single chain wherein a domain $V_L$ and $V_H$ are linked by a connecting peptide promoting the association between the two domains so as to form a linkage site for the antigen. Examples of possible forms and structures of the antibodies are described in Holliger&Hudson (2006) Nature Biotechnology 23(9): 1126-1136; Carter (2006) Nature Reviews Immunology 6:343:357.

In case the ligand is an antibody, however alternative embodiments can be provided such as a human, humanized, murine, chimeric, rabbit, sheep antibody or however of any origin provided that it is capable of recognizing and binding at least an epitope of the AMH hormone. Under the term "humanized" an antibody is meant comprising a human framework region (FR) and one or more regions determining the complementarity (CDR) of not human origin, for example murine. In a preferred embodiment of the invention, the antibody is of human origin. By purely way of example an antibody able to recognize the human AMH is the one commercialized by ABCAM, # cat. ab103233, MIS Antibody(C-20): sc-6886 of Santa Cruz; antibody against AMH # cat (MM0475-7H26) of Novus Biologicals; hormone against AMh # cat AM05878SU-N, of Acris Antibodies.

Furthermore, the antibody, as well as the receptor able to bind AMH, can be both a recombinant protein and a protein usually present in nature.

Under recombinant protein a molecule is meant which is produced in organisms and host cells which do not produce naturally the protein of interest, for example either an anti-AMH antibody or an AMH receptor.

The antibody can be both a monoclonal and a polyclonal antibody or, as it is known to the person skilled in the art, an antibody with a single binding specificity or obtained from antibodies produced by different colonies of B lymphocytes.

The ligand of the AMH subject of the present invention is an isolated ligand labeled so as to be directly detected by means of magnetic resonance imaging in the endometriosis lesions.

Under the term "isolated" in the present invention ligands in substantially free form are meant, for example in case of ligands present in the cells, free from any cellular material. In other words, in case the ligand, for example, is an AMH receptor, such receptor will be in a different form from that in which it is in nature, that is without interactions with cellular components, such as for example, the plasma membranes thereto it is usually associated. In case of an anti-AMH antibody, instead, it will be free from antibodies having different antigenic specificity.

In particular, the detection of the marked ligand by means of magnetic resonance imaging can be performed by using techniques such as for example, and without being limited thereto: echography, radiography, computed tomography, nuclear magnetic resonance, tomography with emission of positrons, scintigraphy or however any other imaging method useful to detect the antibody of the invention.

Such techniques are well known to the person skilled in the art and therefore do not require herein further experimentation. A description of the magnetic resonance imaging techniques useful to the purpose of the present invention is however present in Sutton's Textbook of Radiology & Imaging 7th Edition, published by Churchill Livingstone.

For the purpose of detection, the ligand can be labeled by using any agent suitable for detection by means of magnetic resonance imaging and, as it will be understood, the type of agent used to label the ligand mainly will depend upon the type of techniques which will be chosen for showing the endometriosis lesions. Generally, the ligand can be labeled with at least one of the agents selected from the group consisting of: paramagnetic contrast agents, iodized contrast agents, intravenous contrast agents, and radioisotopes.

Purely by way of example and not for limiting purposes, the paramagnetic contrast agents can be chosen among: gadolinium or manganese; the iodized contrast agents can be chosen among: ioexolo, ioversolo, iopromide, iopamidolo, iodixanolo; the intravenous contrast agents can be chosen among: sulphur hexafluoride; the radioisotopes can be chosen among: Tecnezio 99, Iodine 131, Thallium 201, Iodine 125, Fluorine 18, and Carbon 14.

In particular, for Nuclear Magnetic resonance, the ligand of the invention can be labeled for example with: gadodiamide (Omniscan®), gadobenic acid (Multihance®), gadobutrol (Gadovist®), gadofosveset (Vasovist®), gadopentetic acid (Magnevist®), gadoteric acid (Dotaren®), gadoteridol (Prohance®), and gadoxetic acid (Primovist®). For detection by means of computerized tomography, iodized agents can be used such as: monomers such as ioexolo (Omnipaque®), ioversolo (Optiray®), iopromide (Ultravist®), iopamidol (for example Lopamiro®), or dimers such as iodixanol (Visipaque®). For the echography, the ligand of the invention for example can be labeled with intravenous contrast agents constituted by microbubbles of sulphur hexafluoride or other graphic contrast agents for ultrasounds.

In a preferred embodiment of the invention, the ligand is a polyclonal or monoclonal antibody able to recognize and link the AMH of human origin labeled with gadolinium. The labeling and conjugation of a protein with a detecting agent, such as those shown above, nowadays is performed by means of techniques well known to the person skilled in the art. By way of example, the methods which can be used for conjugating or marking the ligand of the invention are described in Kuriu Y et al. Monoclonal antibody conjugated to gadolinium as a contrast agent for magnetic resonance imaging of human rectal carcinoma. J Surg Oncol. 2006 Aug. 1; 94(2):144-148; and Molecular Imaging and Contrast Agent Database (MICAD) [Internet]. Bethesda (Md.): National Center for Biotechnology Information (US); 2004-2013 (available in: http://www.ncbi.nlm.nih.gov/books/NBK23053/).

As shown previously, the herein described ligand demonstrated to be useful in particular to the purpose of localizing and/or evaluating the entity of the endometriosic lesions directly in vivo in a patient suffering from, or supposed suffering from, endometriosis. Under endometriosis lesion, analogously to what reported in literature, the presence of endometrial tissue, both glandular and stromal tissue, outside the cavity of uterus is meant. In the specific case, the anti-AMH antibody of the invention allows detecting in vivo both cystic and connective solid endometriosis lesions. The evaluation of the entity of the lesions, in this case, substantially relates to the analysis to the purposes of diagnosing or treating the size of the foci of the endometriosis disease. The size of the endometriosis lesions can be very variable and in case of neoformed lesions the sizes can be so reduced that they do not allow the localization thereof by the physician. Advantageously the ligand of the invention allows displaying even endometriosis lesions with diameter smaller or larger than 1 centimeter and 0.5 centimeters. Under evaluation of the entity of the endometriosis lesions herein the physician's determination of the sizes and/or the spreading level of the disease foci is meant in order to understand the endometriosis progress stage and, in case, to define the best therapeutic approach to be followed.

The subject of the present invention then is also a formulation to be used in an in vivo method for localizing and/or evaluating the entity of the endometriosic lesions in a patient comprising at least a ligand of the invention and at least a pharmaceutically acceptable carrier and/or excipient. In a preferred embodiment the formulation is administered to the patient wherein one wants to localize and/or evaluate the entity of the endometriosis lesions, by injection or infusion, or even in case by means of oral administration. A pharmaceutically acceptable carrier can be chosen, for example, among buffer aqueous solutions, sterile water, balanced saline physiological solutions, ions, and additives.

Purely by way of example, the buffer aqueous solutions can be chosen among tris (hydroxyethyl) amino methane and the salts, phosphate, citrate and bicarbonates; the balanced ionic solutions, instead, can be selected among chlorides and bicarbonates of cations chosen among Ca, Na, K, Mg and other halides, carbonates, sulphates, phosphates and Na, K, Mg and Ca; the excipients can be chosen among glycerol, polyethylene glycol, and dextran. In any case, the carriers and the excipients which can be comprised in the formulation of the invention can be chosen among those commonly known and considered useful by the person skilled in the art for the present invention.

The subject of the present invention is also a kit for localizing and/or evaluating the in vivo entity of endometriosis lesions in a patient comprising at least a ligand of the invention or a formulation as above described and means useful for the administration of said ligand or said formulation to the patient. Purely by way of example, such means can comprise physiological solutions, needles, syringes, sterilizing solutions, etc. Furthermore, herein also an in vivo method is described for localizing and/or evaluating the in vivo entity of the endometriosis lesions in a patient comprising a passage of administering the ligand or the formulation of the invention to the patient itself. As already designated previously, under localization the possibility of detecting precisely the site wherein there is the endometriosis lesion is meant, whereas under evaluation substantially the analysis of the sizes of the localized lesions is referred to. From this point of view, then, the in vivo method can even include an operating passage wherein the subject, thereto the ligand or the formulation of the invention was administered, is subsequently subjected to a technique of magnetic resonance imaging. By pure way of example and not for limitative purposes, such techniques can be: echography, radiography, computed tomography, nuclear magnetic resonance, tomography with emission of positrons.

The just described method can be performed, if the person skilled in the art can consider to be useful, even on in vitro tissue samples and in this case then the in vitro method for localizing and/or evaluating the entity of the endometriosis lesions will include a step of incubating a tissue sample, obtained from the patient under analysis, with a ligand or a formulation of the invention. In a way analogous to what described above, the sample can be subsequently subjected to a technique of magnetic resonance imaging with the purpose of allowing to show the site and the sizes of the endometriosic disease foci.

EXAMPLES

Example 1. In Vivo Expression of AMH Hormone in Endometriosis Lesions by Means of Immunohistochemical Methods This experiment represents the first scientific demonstration of the fact that the AMH hormone is clearly and abundantly expressed in the endometriosis lesions, both in the glandular and in the stromal component. For this demonstration, collections of tissue were performed at the subperitoneal level from 10 patients affected by endometriosis; the tissues were fixed in 10%-buffered paraformaldehyde, included in paraffin and stained with Hematoxylin and Eosin to highlight the glandular and stromal structures of endometriosis. On stored sections, immediately subsequent to the ones stained with Hematoxylin and Eosin, immunohistochemical staining were performed, by using with proper dilutions an antibody specific for AMH (anti-AMH antibody of ABCAM, # cat. ab103233) with the dilution of 1 to 100, the ABC system, and the staining with Diaminobenzidine to detect the antigen-antibody complexes. Such experiment allowed demonstrating that the AMH hormone is constantly and abundantly expressed in the glandular and stromal component of the endometriosis lesions. FIG. 1 shows two examples of such expression.

Example 2. Xenotransplant of Human Endometriosic Tissue in Nude Mice

Figure 4:
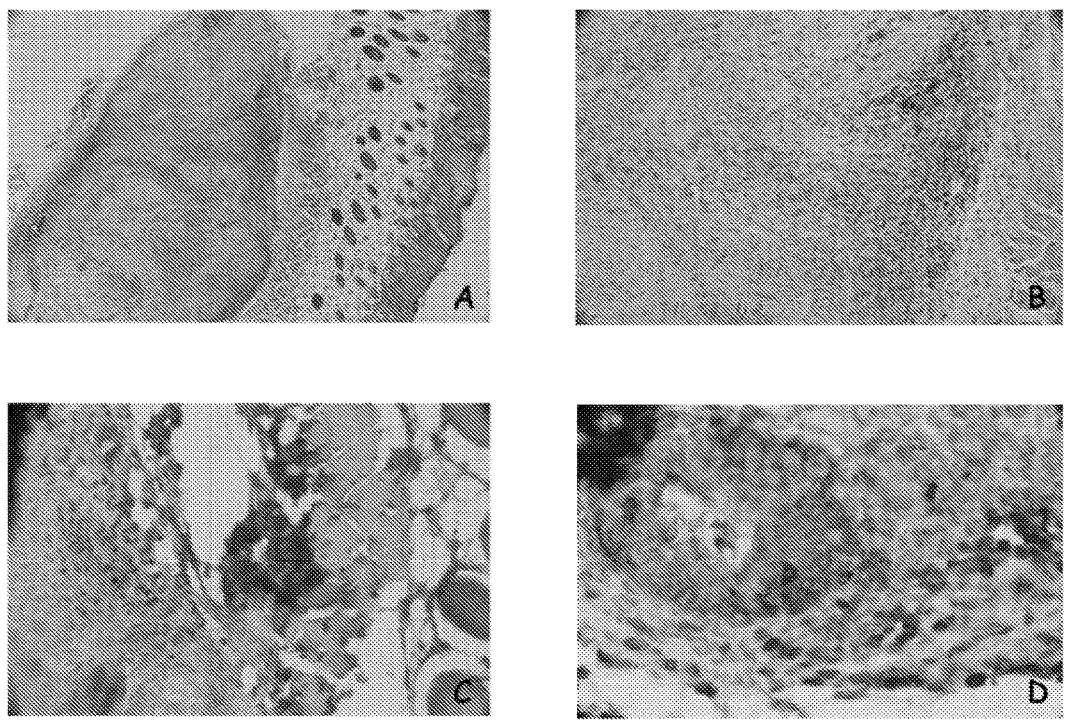

Fragments of human connective solid endometriosic tissues (max diameter about 3 mm) collected from two different patients during surgical removal operation by laparoscopic way were transplanted subcutaneously in the left side of two female nude mice. After implanting endometriosis tissue, performed in total anaesthesia, the small female mice were stabled for two weeks with food and water ad libitum and, limited to the first week, with antibiotic therapy (5% enrofloxacin in the beverage water). The imaging evaluation was performed by means of using a 0.2-Tesla magnetic resonance for veterinary use. The small female mice were sedated with tiletamine+zolazepam+xylazine in order to be able to perform the imaging studies. After being positioned in the apparatus, total-body and local studies were performed for the abdominal area with sections of 2 mm. Subsequently the small female mice were removed from the apparatus for a second administration of sedative and in order to be able to perform the intravenous inoculation (tail vein) of the antibody (10 µl of a 0.2 mg/ml concentrated solution of anti AMH antibody conjugated with gadolinium). The small female mice were repositioned, and total-body and loco-regional studies were performed. Both in the total-body study (FIG. 2) (wherein subcutaneous captation is found with residue of antibodies in the inoculation site in the caudal vein) and in some cross sections (FIG. 3), antibody capture is highlighted in the site of transplanting the endometriosis tissue. In particular, in the cross section of an animal before the treatment, the subcutaneous mass not having signs of capture is found. After the experiment, the animals were brought in animal house and sacrificed to explant the ectopic tissue. Such tissue was then analysed with histological and immunohistochemical examination. These examinations confirmed that the transplant histological aspect was that of a connective solid endometriosis tissue. At last, by means of immunohistochemical examination, performed by using the same method shown before, it was demonstrated that such transplanted tissue expressed CD10 (marker of endometriosis tissue) and the codifying protein for AMH (FIG. 4).

The invention claimed is:

1. An in vivo method for diagnosis of endometriosis comprising localizing and/or evaluating endometriosic lesions in a patient by administration of an isolated ligand of anti-Mullerian hormone consisting of an anti-Mullerian hormone antibody or the receptor of type II of anti-Mullerian hormone (MISIIR) to said patient, said ligand being labeled to be directly detected by an imaging technique.

2. The in vivo method according to claim 1, wherein said antibody is human, humanized, murine, or chimeric.

3. The in vivo method according to claim 1, wherein said antibody is a polyclonal or monoclonal antibody.

4. The in vivo method according to claim 1, wherein said ligand is directly detected by echography, radiography, computed tomography, nuclear magnetic resonance, tomography with emission of positrons, or scintigraphy.

5. The in vivo method according to claim 1, wherein said ligand is labeled with at least one agent selected from the group consisting of: paramagnetic contrast agents, iodized contrast agents, intravenous contrast agents, and radioisotopes.

6. The in vivo method according to claim 5, wherein
said paramagnetic contrast agent is gadolinium or manganese; or
said iodized contrast agent is ioexolo, ioversolo, iopromide, iopamidolo, or iodixanolo; or
said intravenous contrast agent is sulphur hexafluoride; or
said radioisotope is Tecnezio 99, Iodine 131, Thallium 201, Iodine 125, Fluorine 18, or Carbon 14.

7. The in vivo method according to claim 1, wherein said lesions are endometriosis neoformations with diameters smaller than 1 centimeter.

8. The in vivo method according to claim 7, wherein said lesions are endometriosis neoformations with diameters larger than 0.5 centimeter.

* * * * *